(12) United States Patent
Jalde et al.

(10) Patent No.: US 9,055,880 B2
(45) Date of Patent: Jun. 16, 2015

(54) METHOD AND APPARATUS FOR DETERMINING AN IN VIVO POSITION OF AN ESOPHAGEAL CATHETER

(75) Inventors: Fredrik Jalde, Bromma (SE); Georgios Psaros, Tullinge (SE)

(73) Assignee: Maquet Critical Care AB, Solana (SE)

(*) Notice: Subject to any disclaimer, the term of this patent is extended or adjusted under 35 U.S.C. 154(b) by 1027 days.

(21) Appl. No.: 13/140,720

(22) PCT Filed: Dec. 18, 2008

(86) PCT No.: PCT/SE2008/051514
§ 371 (c)(1),
(2), (4) Date: Oct. 26, 2011

(87) PCT Pub. No.: WO2010/071520
PCT Pub. Date: Jun. 24, 2010

(65) Prior Publication Data
US 2012/0035452 A1  Feb. 9, 2012

(51) Int. Cl.
*A61B 5/06* (2006.01)
*A61B 5/0488* (2006.01)
*A61B 5/00* (2006.01)
*A61N 1/36* (2006.01)
*A61N 1/05* (2006.01)

(52) U.S. Cl.
CPC ............ *A61B 5/04884* (2013.01); *A61B 5/065* (2013.01); *A61B 5/06* (2013.01); *A61B 5/42* (2013.01); *A61N 1/3601* (2013.01); *A61N 1/0517* (2013.01)

(58) Field of Classification Search
CPC ............ A61M 2230/08; A61M 2230/60; A61M 2230/005; A61M 16/0051; A61B 5/0488; A61B 5/0421; A61B 5/065; A61N 1/0517

USPC .......... 600/372, 373, 380, 424, 547, 550, 554
See application file for complete search history.

(56) References Cited

U.S. PATENT DOCUMENTS

| | | | |
|---|---|---|---|
| 5,178,149 A * | 1/1993 | Imburgia et al. | 600/463 |
| 6,266,549 B1 * | 7/2001 | Melnikoff et al. | 600/380 |
| 6,360,740 B1 | 3/2002 | Ward et al. | |
| 6,438,400 B1 * | 8/2002 | Beard et al. | 600/380 |
| 6,690,963 B2 * | 2/2004 | Ben-Haim et al. | 600/424 |
| 6,788,967 B2 * | 9/2004 | Ben-Haim et al. | 600/424 |
| 7,634,311 B2 * | 12/2009 | Blomberg et al. | 600/546 |
| 7,689,275 B2 * | 3/2010 | Blomberg et al. | 600/546 |

(Continued)

FOREIGN PATENT DOCUMENTS

| | | |
|---|---|---|
| CN | 88107124.2 | 5/1990 |
| WO | 2006/062710 | 6/2006 |

*Primary Examiner* — Sean Dougherty
(74) *Attorney, Agent, or Firm* — Schiff Hardin LLP

(57) ABSTRACT

In a method and an apparatus for determining the position of an esophageal catheter that is inserted into the esophagus of a patient, the catheter having a number of electrodes, muscular activity of the diaphragm is stimulated by applying a stimulus signal that produces a myoelectrical signal in the diaphragm having a well-defined peak at a specific point in time. The myoelectrical signal is detected by respective pairs of electrodes of said catheter, and the electrode pair or pairs that detected the signal having the highest amplitude at the specific point in time is identified. If this electrode pair or these electrode pairs that detected the signal with highest amplitude are not located approximately at the middle of the catheter, an indication is emitted that the position of the catheter should be adjusted.

13 Claims, 2 Drawing Sheets

(56) References Cited

U.S. PATENT DOCUMENTS

| | | | |
|---|---|---|---|
| 8,256,419 B2* | 9/2012 | Sinderby et al. | 128/204.23 |
| 8,285,399 B2* | 10/2012 | Van Bommel et al. | 607/124 |
| 8,364,455 B2* | 1/2013 | Blomberg et al. | 703/11 |
| 8,478,412 B2* | 7/2013 | Ignagni et al. | 607/42 |
| 8,485,980 B2* | 7/2013 | Sinderby et al. | 600/484 |
| 8,676,323 B2* | 3/2014 | Ignagni et al. | 607/42 |
| 2002/0165448 A1* | 11/2002 | Ben-Haim et al. | 600/424 |
| 2003/0079750 A1* | 5/2003 | Berthon-Jones | 128/204.18 |
| 2003/0097167 A1* | 5/2003 | Friedman | 607/124 |
| 2003/0188748 A1* | 10/2003 | Sinderby et al. | 128/204.21 |
| 2006/0116564 A1* | 6/2006 | Mintchev et al. | 600/350 |
| 2006/0122661 A1 | 6/2006 | Mandell | |
| 2007/0276280 A1* | 11/2007 | Blomberg et al. | 600/546 |
| 2008/0121231 A1* | 5/2008 | Sinderby et al. | 128/204.21 |
| 2008/0275360 A1* | 11/2008 | Fandriks | 600/546 |
| 2008/0308104 A1* | 12/2008 | Blomberg et al. | 128/204.23 |
| 2009/0036769 A1* | 2/2009 | Zdeblick | 600/424 |
| 2009/0084382 A1* | 4/2009 | Jalde et al. | 128/204.23 |
| 2010/0116274 A1* | 5/2010 | Jalde | 128/204.23 |
| 2010/0180896 A1* | 7/2010 | Blomquist et al. | 128/204.23 |
| 2014/0275991 A1* | 9/2014 | Potter et al. | 600/424 |

* cited by examiner

METHOD AND APPARATUS FOR DETERMINING AN IN VIVO POSITION OF AN ESOPHAGEAL CATHETER

BACKGROUND OF THE INVENTION

1. Field of the Invention

The present invention relates to a method of determining the position of a catheter in a patient's esophagus, a control unit for use with a ventilator, and a computer program product for use in such a control unit.

2. Description of the Prior Art and Related Applications

It is known in the art to use myoelectrical or neuroelectrical signals from a patient to control the function of a ventilator providing breathing support to the patient. U.S. Pat. No. 5,820,560 and U.S. Pat. No. 6,588,423 both disclose methods and devices for triggering ventilatory support to a patient using a myoelectrical signal obtained from the diaphragm. U.S. Pat. No. 5,671,752 discloses a method and a device for registering the myoelectrical activity of the diaphragm by means of an esophageal catheter having an array of electrodes. The signals from such a catheter can be used as the myoelectrical signal to control ventilator function. EP 1 091 780 discloses the use of a neuroelectrical signal picked up, for example, from the phrenic nerve to control a ventilator.

A problem when obtaining a myoelectrical signal from the diaphragm is positioning of the catheter within the patient's esophagus. To obtain a proper signal some of the electrodes of the catheter should be placed above the diaphragm and some below it. There is a possibility that the catheter will be inserted too far, or not be inserted far enough. In both cases, the catheter will detect a weak signal, or may not capture any signal at all. Alternatively, the catheter may capture myoelectrical signals from other muscles instead of, or in addition to the signal from the diaphragm. Hence, it is difficult to obtain an optimal catheter position and the ventilator may have to work in pneumatic triggering mode if the signal is too weak.

There are some problems associated with methods based on the registration of the EMG signal from the diaphragm.

- There may not be an EMG signal present, for example if the patient is sedated or has no breathing activity of his own for other reasons.
- The EMG signal may be very weak and/or difficult to detect, for example because of disturbances caused by breathing support provided to the patient.
- There is a risk that other myoelectric signals resembling that of the diaphragm but originating from other muscles are mistaken for signals from the diaphragm. Such signals may come, for example, from the abdominal muscles.

Co-pending application No PCT/EP2007/054149 discloses a method of positioning the catheter based on the ECG component that will always be present in a myoelectrical signal from the diaphragm. In this application, the damping of the ECG signal caused by the diaphragm is used. The ECG signal components from different electrode pairs are determined and compared and the difference in amplitude of the ECG signal between different electrode pairs is used to determine the position of the diaphragm relative to the electrode pairs. The greatest damping between two neighbouring electrode pairs should be caused by the diaphragm being positioned between these two electrode pairs. This method is predominantly based on the registration and comparison of the QRS complex of the ECG signal.

Co-pending Swedish patent application No. 0850076-1 discloses a method utilizing the presence of the p wave of the ECG signal. Since the damping of the p wave is very strong with increasing distance from the heart, any electrode pair picking up a p wave must be located fairly close to the heart's atria, well above the diaphragm.

SUMMARY OF THE INVENTION

It is an object of the invention to determine the position of an esophageal catheter inserted in a patient, in relation to the patient's diaphragm.

This object is achieved by a method of determining the position of an esophageal catheter inserted into the esophagus of a patient, said catheter having a number of electrodes arranged to pick up a myoelectrical signal, including the following steps:

- stimulating the muscular activity of the diaphragm at a specific point in time or period, and detecting resulting signals respectively with different pairs of said electrodes
- supplying the signals detected by the respective electrode pairs of the esophageal catheter at the specific point or period in time to a computerized processor, and
- in the processor, automatically determining which of said electrode pairs detected a signal with the highest amplitude.

The object is also achieved by an apparatus for determining the position of an esophageal catheter inserted into the esophagus of a patient for picking up myoelectric signals from the patient, including

- at least one stimulating electrode arranged to stimulate the muscular activity of the diaphragm by applying a stimulus signal,
- a catheter having a number of electrodes that respectively detect a myoelectrical signal resulting from the stimulation of muscular activity by the stimulus signal,
- a registering unit that registers the signals detected by respective pairs of the electrodes of the esophageal catheter at the specific point in time and the stimulus,
- a control that operates the stimulating electrode to cause stimulating the electrode to stimulate the muscular activity at a specific point in time, and that automatically determines which of said electrode pairs detected a signal with the highest amplitude at the specific point in time, based on the signals received by the registering unit.

The object is also achieved by a non-transitory computer-readable storage medium encoded with programming instructions for controlling an apparatus for determining the position of an esophageal catheter inserted into the esophagus of a patient, the catheter having a number of electrodes arranged to pick up a myoelectrical signal, and at least one electrode arranged to stimulate the muscular activity of the diaphragm, when the storage medium is loaded in a control unit of the apparatus, the programming instructions cause the apparatus to:

- stimulate the muscular activity of the diaphragm at a specific point in time, register the signals detected by respective pairs of the esophageal catheter at the specific point in time,
- determine which of the electrode pairs detected the stimulus signal with the highest amplitude.

By stimulating the diaphragm and registering the signal at the time of stimulation it is ensured that the registered signal really is the signal from the diaphragm and not another bio-electrical signal that resembles that of the diaphragm. By registering the signals from all electrode pairs of an esophageal catheter at the time of stimulation, the ones registering the strongest signal can be determined. This electrode pair or these electrode pairs will be the ones closest to the diaphragm. In this way the position of the catheter relative to the diaphragm can be determined and adjusted as desired.

The stimulus signal may be applied transcutaneously or subcutaneously, using any known method and suitable electrodes for applying the signal in the desired way.

The stimulus signal may be applied to a nerve controlling the function of the diaphragm, such as the phrenic nerve or to the diaphragm itself.

In a preferred embodiment the control unit determines if the electrode pairs that record the strongest stimulus signal are located in or close to the middle of the catheter and, if they are not, indicate that the catheter should be adjusted. This is preferably achieved by means of a computer program algorithm.

This will provide a direct feedback to an operator that the catheter position should be adjusted. As a response to this, the method may include the step of adjusting the position of the catheter in the appropriate direction to bring the middle electrode pairs closer to the diaphragm.

The method steps may be repeated at regular or irregular time intervals. This will enable continuous monitoring of the catheter's position. Preferably the control unit is arranged to repeat the method steps related to stimulating, recording the signals and determining the position of the electrodes repeatedly.

The stimulation of the diaphragm may be performed by invasive or non-invasive methods. Non-invasive methods have the advantage of being easier to perform and causing less discomfort to the patient. A non-invasive method would be to stimulate the phrenic nerve from the outside of the neck, but this entails a risk of stimulating another nerve instead of, or in addition to, the phrenic nerve, which may cause undesired effects.

Electrical stimulation may be applied non-invasively using electrodes applied to the skin surface. Percutaneous electrodes have also been developed, which can be left in place over a period of time to allow specific reproducible stimulation patterns. The best site for transcutaneous stimulation of the phrenic nerve is on the neck a few cm above the clavicle, since this site is as far away from the vagus nerve as possible. Unwanted stimulation of the vagus nerve can cause severe bradycardia and other negative effects.

Invasive methods include invasive stimulation of the phrenic nerve as well as direct invasive stimulation of the diaphragm itself. Such methods have greater impact on the patient's body but offer better control of what nerve or muscle to stimulate. Several types of implanted electrodes can be found. Invasive electrodes can be placed using several different techniques, including neck incisions, thoracoscopic procedures or thoracotomy. For example, electrodes available from Avery Labs incorporate an antenna placed immediately under the skin, which allows activation of the electrode through intact skin.

European Patent application 1 389 442 discloses a neural probe having a number of electrodes, which may be used to stimulate nerve cells. Another manufacturer of suitable stimulation electrodes for diaphragm pacing is Synapse Biomedical. Atrotech Oy manufactures a phrenic nerve stimulator.

The method according to the invention may be combined with other known methods for positioning the esophageal catheter. For example, the method of co-pending application No. PCT/EP2007/054149 might be used first to position the catheter. Then the inventive method may be used to adjust the catheter position. The position may be adjusted so that the electrodes located in the middle of the catheter have the highest registered EMG signals. The NEX method may also be used for a first positioning of the catheter.

The inventive procedure may also be used during operation, to ensure that the catheter position has not changed too much, for example because of the patient's movements.

The programming instructions of the storage medium may also cause the control unit to present the determined position of the catheter to the user on a display, for example, the display of the ventilator. This will assist the operator in determining the position of the catheter correctly.

DESCRIPTION OF THE PREFERRED EMBODIMENTS

Figure 1A:
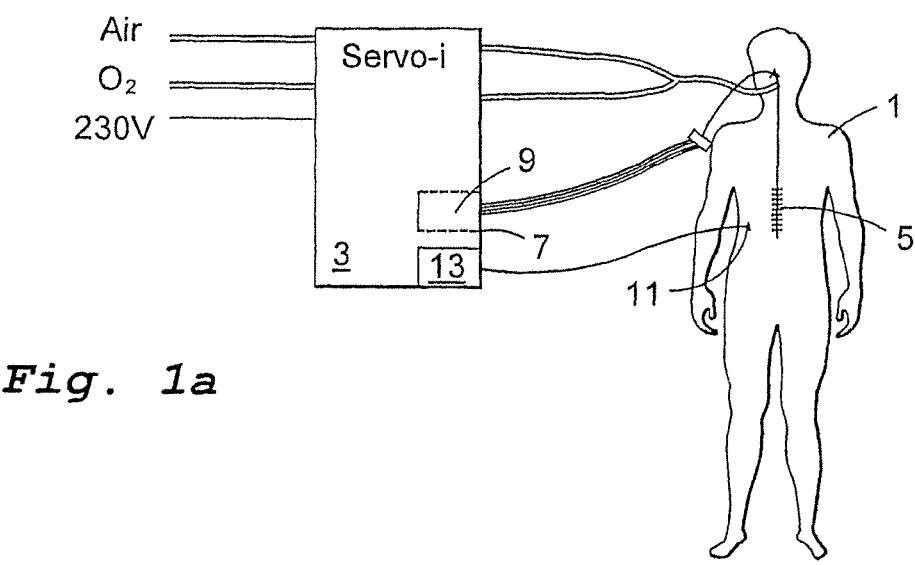
FIG. 1 illustrates a patient with an esophageal catheter used to control a ventilator.

FIG. 1 is a schematic overview of a patient 1 connected to a ventilator 3 and having an esophageal catheter 5 inserted in order to record a myoelectric signal from the diaphragm. Instead of the ventilator, the inventive idea could be used with a device arranged to monitor the signal from the esophageal catheter. This myoelectric signal is fed to a control input of the ventilator 3 to control the ventilation function of the patient 1. The catheter 5 has a number of electrodes, for example, nine electrodes placed equidistantly in an array along the catheter to produce 8 subsignals, each subsignal being a difference signal between two neighbouring electrodes. The subsignals will be received by receiving means 7 and processed in a control unit 9 in the ventilator to produce the overall signal that can be used to control the ventilator. To this end, the control unit 9 is loaded with at least one non-transitory computer-readable storage medium encoded with programming instructions that control the ventilator to perform the calculations and other relevant functions.

The registration of a myoelectric (EMG) signal from the diaphragm may not always be successful. As for any bioelectric signal, the EMG signal recorded from the diaphragm will comprise disturbance, in particular from the heart, but also from other muscles such as abdominal muscles. If the catheter is inserted much too far into the patient, the disturbing signals may constitute the largest part of the signal picked up by some or all the electrode pairs. In this case, there is a risk that the control signal provided to the ventilator is not related to the patient's breathing activity. In other cases, the patient may exhibit no breathing activity, or too little breathing activity to enable a proper registration. The breathing activity can be reduced, for example, because of illness or sedation.

Even if the catheter is initially positioned in the right place it may be moved up or down within the patient's esophagus because of the patient's breathing activity or other movements, so that after a while the diaphragm activity is not registered in the right way.

According to the invention, therefore, the arrangement of FIG. 1 also includes at least one electrode 11 for stimulating the diaphragm. The electrode 11 may be of any kind suitable for stimulating nerve or muscle cells, depending on where the stimulus is provided. The stimulus may be provided transcutaneously or subcutaneously to the phrenic nerve, or directly to the diaphragm. The electrode 11 may be controlled by an electrode control unit 13, which may be positioned in the ventilator 3, as shown in FIG. 1. It may also be a separate unit. If it is part of the ventilator, it may be integrated with the control unit 9 or it may be a separate unit. The electrode control unit 13 typically comprises a computer program for controlling the stimulation function.

Figure 1B:
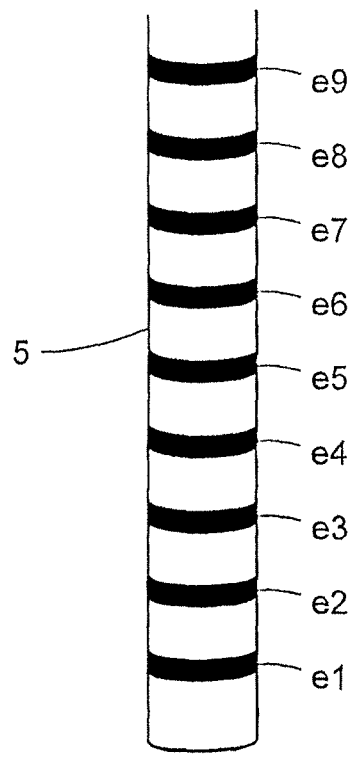

FIG. 1b shows a schematic example of an esophageal catheter 5 like the one shown in FIG. 1a. The catheter has nine electrodes, numbered e1, e2, . . . , e9 in the Figure. Each channel is recorded as the difference signal between two adjacent electrodes, that is, between e1 and e2, between e2 and e3, etc. Hence, the uppermost channel will be the one recorded between the two uppermost electrodes e8 and e9, also referred to as the uppermost electrode pair. Ideally, the catheter 5 should be positioned in such a way that the electrodes e4, e5, e6 located in the middle of the catheter 5 should be near the diaphragm, in order to pick up the best signal from the diaphragm. It should be understood that this configuration of the catheter is only an example. It is, however, usually suitable to place the electrodes in the middle of the catheter near the diaphragm.

Figure 2:
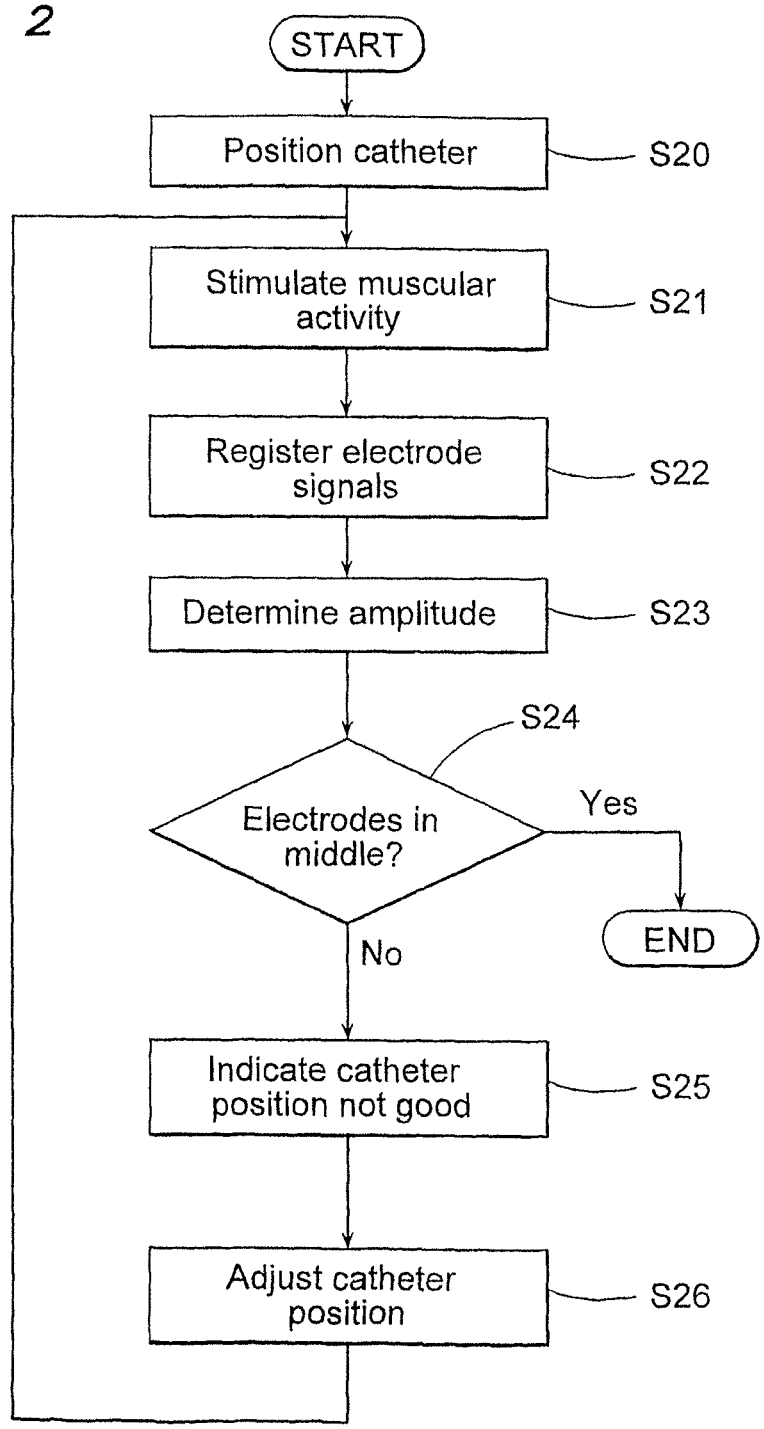
FIG. 2 is a flow chart of a method according to an aspect of the invention.

A method according to an aspect of the invention comprises the steps shown in FIG. 2:

Step S20: Position the catheter in the patient's esophagus. As discussed above, a number of methods exist for finding an appropriate position for the catheter.

Step S21: Stimulate the muscular activity of the diaphragm at a specific point or period in time by applying a stimulus signal either to a nerve controlling the function of the diaphragm, or to the diaphragm itself. The stimulus signal may be applied as a short pulse at a point in time or over a period of time, typically during one breath.

Step S22: Register the signals recorded by the electrode pairs of the esophageal catheter at the specific point or period in time.

Step S23: Determine which electrode pairs record the stimulus signal with the highest amplitude.

Step S24: Are the electrode pairs that record the strongest stimulus signal located in or close to the middle of the catheter? If yes, end of procedure; if no, go to step S25.

Step S25: Indicate that the catheter is not in an optimal position. To do this, the control unit 9 will indicate the position of the catheter on a display. The control unit may also issue an explicit message that the catheter position should be adjusted, for example, on the display, or through an audio alarm.

Step S26: Adjust the position of the catheter in the appropriate direction to bring the middle electrode pairs closer to the diaphragm. This will normally be done manually by health care personnel. Return to step S21.

If the answer in step S24 is yes, this indicates that the catheter is in an appropriate position for registering the EMG signal from the diaphragm. By repeating the procedure at regular or irregular time intervals, the position of the catheter can be monitored over time. It may be advantageous to wait for a certain period of time and then repeat the procedure to ensure that the catheter remains in the right place and to adjust it if it moves. The algorithm may also be performed in other situations, for example, when the EMG signal ceases or deteriorates dramatically, or if it is detected that ventilation correctly with the patient's breathing efforts. The latter situation is discussed in co-pending Application No. PCT/SE2007/051048.

The stimulation performed in step S21 can be carried out to provide a well defined EMG signal from the diaphragm when the spontaneous activity of the diaphragm is too weak to be recorded properly. It may also be used if there is normal activity of the diaphragm, to provide a well-defined peak of the EMG signal at a specific point in time, to ensure that the signal picked up by the electrodes is really the signal from the diaphragm and not a disturbing signal from some other muscle.

The timing of the stimulation performed in step S21 should be determined based on a number of factors. From a technical point of view a period with no disturbances from other signals, such as EMG and ECG, might be preferable, to enable an unambiguous detection of the stimulus signal. If the patient has any spontaneous breathing activity, from a clinical point of view it would be suitable to synchronize the stimulus signal with the patient's inspiration phase. The point in time at which the stimulus signal is applied should be known in order to detect when the stimulus signal will be detected.

In step S24, if the initial positioning of the catheter was unsuccessful it may be that the catheter is positioned in such a way that none of the electrodes are measuring on the diaphragm. In this case, the catheter should be adjusted up or down, preferably a distance corresponding to at least the length of the catheter that is covered by the electrodes. Then the procedure should return to step S21.

It may also happen that the amplitude of the stimulus signal is too low for it to be registered properly. If a contraction or a pneumatic triggering can be detected during stimulation, it may be concluded that the amplitude is sufficiently high. If it is determined that the amplitude is too low, the amplitude may be increased until the stimulus signal is detected by the electrodes or causes a response in the patient.

As will be understood, the steps S21-S25 will normally be performed by software running in the control unit 9 of the apparatus. Step S26 will normally be performed by health care personnel.

I claim as my invention:

1. A method for determining a position of an esophageal catheter inserted into the esophagus of a patient, the catheter comprising a plurality of electrodes, comprising the steps of:

artificially stimulating muscular activity of the patient in whom the catheter is inserted, by applying a stimulus signal to the patient, and thereby producing a myoelectrical signal in the patient, said myoelectrical signal having a peak that occurs at a specific point in time due to said stimulus signal;

detecting the myoelectrical signal with respective pairs of said electrodes of said catheter;

registering each myoelectrical signal detected by each of the respective pairs of the electrodes of the esophageal catheter;

automatically determining at least one electrode pair among said electrode pairs of said esophageal electrodes that detected a myoelectrical signal having the highest amplitude at said specific point in time;

automatically determining if said at least one electrode pair that recorded the myoelectrical signal with the highest amplitude is located approximately at a middle of said catheter; and if said at least one electrode pair that detected the myoelectrical signal having the highest amplitude at said specific point in time is not located approximately at the middle of the catheter, automatically generating a humanly perceptible indicator that a position, in the esophagus, of the catheter should be adjusted.

2. A method as claimed in claim 1 comprising applying said stimulus signal to a nerve that controls functioning of the diaphragm of the patient.

3. A method as claimed in claim 1 comprising applying said stimulus signal transcutaneously.

4. A method as claimed in claim 1 comprising applying said stimulus signal subcutaneously.

5. A method as claimed in claim 1 comprising applying said stimulus signal directly to the diaphragm.

6. A method as claimed in claim 1 comprising upon generation of said humanly perceptible signal, manually adjusting the position of the catheter in a direction that brings an electrode of the catheter located at the middle of the catheter closer to the diaphragm of the patient.

7. A method as claimed in claim 1 comprising repeating all of said steps at each of a plurality of separated time intervals.

8. An apparatus for determining a position of an esophageal catheter inserted into the esophagus of a patient comprising:
- an esophageal catheter comprising a plurality of electrodes;
- a stimulation electrode that interacts with the patient to apply a stimulus signal that artificially stimulates muscular activity of the patient in whom the catheter is inserted, to produce a myoelectrical signal in the patient, said myoelectrical signal having a peak occurring at a specific point in time due to said stimulus signal;
- a reception unit that detects the myoelectrical signal with respective pairs of said electrodes of said catheter, and registers each myoelectrical signal detected by each of the respective pairs of the electrodes of the esophageal catheter;
- a processor configured to automatically determine at least one electrode pair among said electrode pairs of said esophageal electrodes that detected a myoelectrical signal having the highest amplitude at said specific point in time, and to automatically determine if said at least one electrode pair that recorded the myoelectrical signal with the highest amplitude is located approximately at a middle of said catheter; and
- if said at least one electrode pair that detected the myoelectrical signal having the highest amplitude at said specific point in time is not located approximately at the middle of the catheter, said processor being configured to automatically generate a humanly perceptible indicator that a position, in the esophagus, of the catheter should be adjusted.

9. An apparatus as claimed in claim 8 wherein said stimulation electrode is configured for placement at a site that causes said stimulus signal to be applied to a nerve that controls functioning of the diaphragm of the patient.

10. An apparatus as claimed in claim 8 wherein said stimulation electrode is configured to apply said stimulus signal transcutaneously.

11. An apparatus as claimed in claim 8 wherein said stimulation electrode is configured to apply said stimulus signal subcutaneously.

12. An apparatus as claimed in claim 8 wherein said stimulation electrode is configured to apply said stimulus signal directly to the diaphragm.

13. A non-transitory computer-readable storage medium encoded with programming instructions, said storage medium being loaded into a processor of an apparatus for determining a position of an esophageal catheter that is inserted into the esophagus of a patient, said catheter comprising a plurality of electrodes, and said apparatus also comprising a stimulating electrode, said programming instructions causing said processor to operate said apparatus to:
- artificially stimulate muscular activity of the patient in whom the catheter is inserted, by applying, via said stimulation electrode, a stimulation signal to produce a myoelectrical signal in the patient, said myoelectrical signal having a well-defined peak occurring at a specific point in time due to said stimulus signal;
- detect the myoelectrical signal with respective pairs of said electrodes of said catheter;
- register each myoelectrical signal detected by each of the respective pairs of the electrodes of the esophageal catheter;
- automatically determine at least one electrode pair among said electrode pairs of said esophageal electrodes that detected a myoelectrical signal having the highest amplitude at said specific point in time;
- automatically determine if said at least one electrode pair that recorded the myoelectrical signal with the highest amplitude is located approximately at a middle of said catheter; and
- if said at least one electrode pair that detected the myoelectrical signal having the highest amplitude at said specific point in time is not located approximately at the middle of the catheter, automatically generate a humanly perceptible indicator that a position, in the esophagus, of the catheter should be adjusted.

* * * * *

UNITED STATES PATENT AND TRADEMARK OFFICE
CERTIFICATE OF CORRECTION

| | | |
|---|---|---|
| PATENT NO. | : 9,055,880 B2 | Page 1 of 1 |
| APPLICATION NO. | : 13/140720 | |
| DATED | : June 16, 2015 | |
| INVENTOR(S) | : Fredrik Jalde et al. | |

It is certified that error appears in the above-identified patent and that said Letters Patent is hereby corrected as shown below:

Title Page, below Item (73) the Assignee's town of "Solana" is spelled incorrectly and should read as "Solna" as inserted below.

TITLE PAGE:

--(73) Assignee: Maquet Critical Care AB, Solna (SE)--

Signed and Sealed this
Twenty-ninth Day of December, 2015

Michelle K. Lee
*Director of the United States Patent and Trademark Office*